US012133937B1

(12) United States Patent
Arinder et al.

(10) Patent No.: US 12,133,937 B1
(45) Date of Patent: Nov. 5, 2024

(54) AIR TREATMENT SYSTEM

(71) Applicant: Triad National Security, LLC, Los Alamos, NM (US)

(72) Inventors: Graham Burton Arinder, Los Alamos, NM (US); Joshua Scott Bort, Los Alamos, NM (US); Eric Richard Olivas, Los Alamos, NM (US); John David Bernardin, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 136 days.

(21) Appl. No.: 17/492,415

(22) Filed: Oct. 1, 2021

Related U.S. Application Data

(60) Provisional application No. 63/086,554, filed on Oct. 1, 2020.

(51) Int. Cl.
*A61L 9/20* (2006.01)

(52) U.S. Cl.
CPC ........... *A61L 9/20* (2013.01); *A61L 2209/134* (2013.01); *A61L 2209/14* (2013.01); *A61L 2209/16* (2013.01)

(58) Field of Classification Search
CPC .. A61L 9/20; A61L 2209/134; A61L 2209/14; A61L 2209/16; A61L 2209/15; A61L 2209/111; A61L 2209/12; G01N 33/0027; F24F 8/22; F24F 8/80; F24F 1/0071; B01D 53/007; B01D 2257/708; B01D 2257/502; B01D 2257/91; B01D 2256/12; B01D 2256/10; B01D 2259/804
See application file for complete search history.

(56) References Cited

U.S. PATENT DOCUMENTS

| 2013/0183214 A1* | 7/2013 | Metteer | F24F 8/20 |
| | | | 422/123 |
| 2017/0252066 A1* | 9/2017 | Worrilow | B01D 53/04 |
| 2019/0054201 A1* | 2/2019 | Zhang | A61L 2/10 |
| 2022/0072185 A1* | 3/2022 | Miller | A61L 9/20 |

OTHER PUBLICATIONS

Heßling et al., "Ultraviolet irradiation doses for coronavirus inactivation-review and analysis of coronavirus photoinactivation studies," *GMS Hygiene and Infection Control*, vol. 15, 8 pages (May 2020).

(Continued)

*Primary Examiner* — Xiuyu Tai
(74) *Attorney, Agent, or Firm* — Klarquist Sparkman, LLP

(57) ABSTRACT

Examples of air treatment systems for use in neutralizing airborne pathogens are disclosed herein. The air treatment systems comprise a housing, an air moving device, and one or more sources of ultraviolet light. An airflow may be directed through the enclosure by the air moving device and exposed to the ultraviolet light sources disposed within the enclosure. In some examples, the air treatment systems include one or more baffles disposed within the enclosure to disrupt the linear flow of air through the enclosure and cause more uniform exposure to the ultraviolet light emitted by the sources of ultraviolet light. Some examples may also include one or more air filters for removing particulate matter.

17 Claims, 11 Drawing Sheets

(56) References Cited

OTHER PUBLICATIONS

The American Society of Heating, Refrigeration, and Air-conditioning Engineers (ASHRAE) is currently recommending a minimum target dose of 1.5 mJ/cm2 using UV-C lamps for disinfection. No Author, N.D., "Filtration / Disinfection," *ASHRAE Technical Resources*, https://www.ashrae.org/technical-resources/filtration-disinfection#uvc, accessed on Dec. 15, 2021, 15 pages.

\* cited by examiner

AIR TREATMENT SYSTEM

CROSS REFERENCE TO RELATED APPLICATION

This application claims the benefit of the earlier filing date of U.S. Provisional Patent Application No. 63/086,554, filed on Oct. 1, 2020, which is incorporated herein by reference in its entirety.

ACKNOWLEDGMENT OF GOVERNMENT SUPPORT

This disclosure was made with government support under Contract No. 89233218CNA000001 awarded by the U.S. Department of Energy/National Nuclear Security Administration. The government has certain rights in the disclosure.

FIELD

The present disclosure relates to air treatment systems for eliminating airborne pathogens, and particularly to air treatment systems employing ultraviolet light to deactivate airborne pathogens.

BACKGROUND

Air circulating within indoor environments, such as hospital rooms, classrooms, office rooms, etc., may contain virus particles, droplets and/or aerosols containing virus particles. Thus, continued circulation of virus-containing air can serve as an infection vector for occupants of those rooms. Accordingly, there is a need for improvements to air treatment systems that deactivate virus-containing droplets/aerosols, and an especially current demand for air treatment systems that address the SARS-COV-2 virus.

SUMMARY

Disclosed herein are air treatment systems having an ultraviolet light source(s) for the deactivation of airborne pathogens. The disclosed air treatment systems can offer superior capacity for removing active pathogens from air by directing an airflow past the light source(s) and subjecting it to sufficient ultraviolet radiation to achieve the deactivation of those pathogens. As such, the air treatment system disclosed herein can, among other things, overcome the challenges related to providing a disinfected air supply to a closed or partially closed environment such as a room or building.

Certain examples concern an air treatment system comprising a housing, an array of ultraviolet light sources disposed within the housing, and an air moving device configured to generate a forced airflow through the housing. The array of ultraviolet lights is configured to provide an irradiance dosage of at least 1.5 mJ/cm$^2$, and to deactivate virus particles in the forced airflow. The housing has an air inlet and an air outlet. The air moving device is configured to generate a forced airflow of at least 1000 cubic feet per minute from the air inlet to the air outlet and past the array of ultraviolet light sources.

Certain examples concern an ultraviolet light air purifier, comprising an ultraviolet light source, an airflow generator, and a plurality of baffles. The ultraviolet light source is configured to emit UV-C light and provide an irradiance dosage of at least 1.5 mJ/cm$^2$. The airflow generator is configured to generate a forced airflow of at least 1000 cubic feet per minute past the ultraviolet light source. The plurality of baffles is configured to introduce turbulence to the forced airflow. Virus particles in the forced airflow are deactivated by the UV-C light emitted from the ultraviolet light source.

Certain examples concern a method for treating air, comprising generating an airflow, introducing the airflow to an air treatment system, and directing the airflow through an enclosed space defined in the air treatment system. The airflow is directed past an array of baffles that impart turbulence to the airflow through the air treatment system. The airflow is exposed to UV-C light within the enclosed space for at least 0.3 seconds, such that at least 99% of virus particles entrained in the airflow are deactivated by the ultraviolet light source, and conveyed out of the air treatment system through an air outlet.

The various innovations of this disclosure can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter.

The foregoing and other objects, features, and advantages of the disclosure will become more apparent from the following detailed description, claims, and accompanying figures.

DETAILED DESCRIPTION

Figure 1:
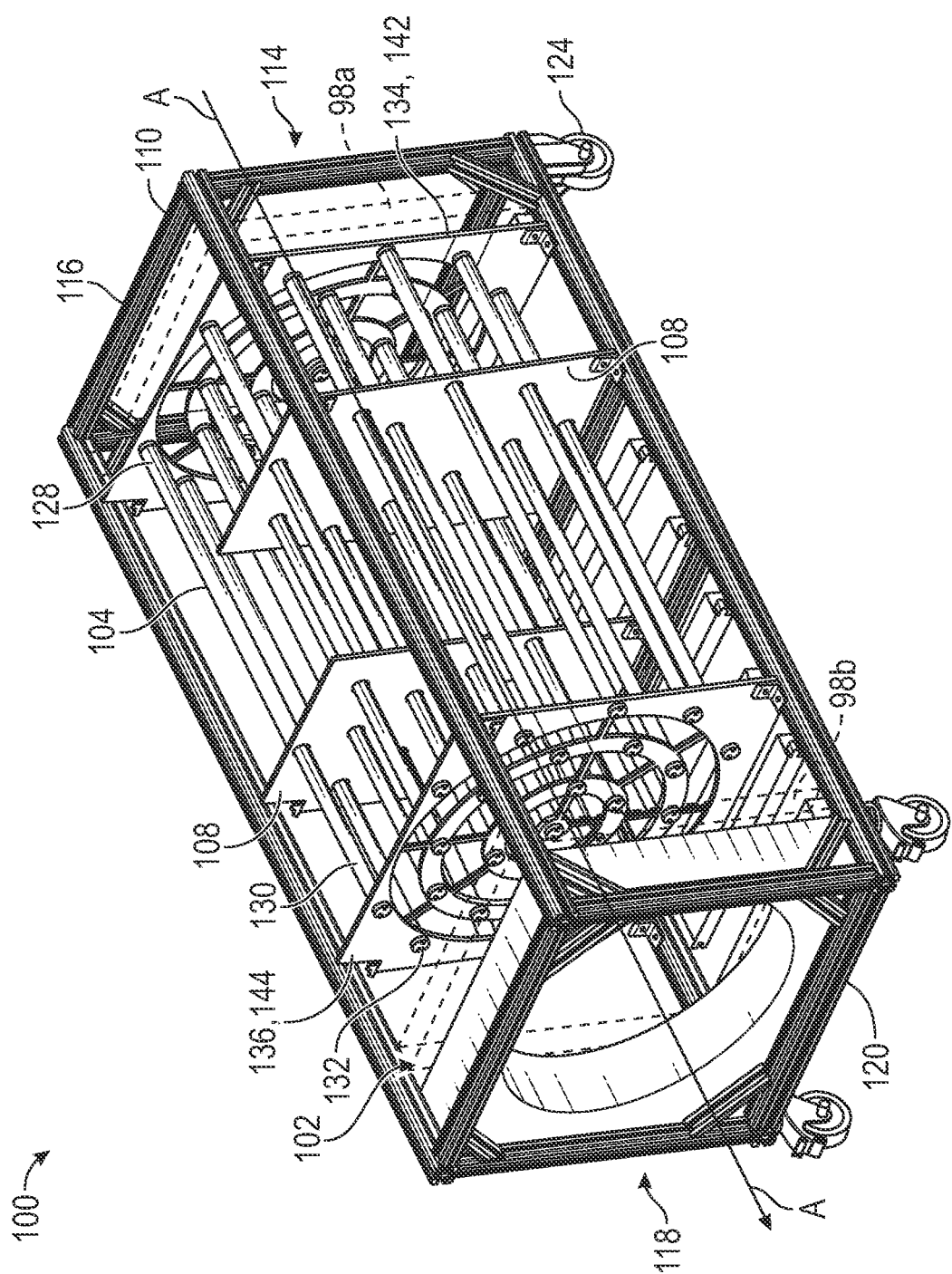
FIG. 1 is a perspective view of an air treatment system according to one embodiment with side panels removed.

Reference will now be made in detail to embodiments of the disclosure, one or more examples of which are illustrated in the drawings. Disclosed herein are various embodiments of air treatment systems, particularly air treatment systems having ultraviolet light sources (also sometime referred to herein as "emitters") capable of deactivating or neutralizing virus particles (i.e., rendering the virus particles non-infectious, such as by preventing future virus replication). The air treatment systems disclosed herein can generally comprise a housing, an airflow generator (also referred to herein as an "air moving device"), and an ultraviolet light source array. In some examples, the air treatment system may further include one or more baffles, one or more air filters, or a combination thereof.

Air in closed or partially closed environments, such as a room or building, can contain various pathogens, including aerosols or droplets with entrained viruses, bacteria, and fungi. Because occupants of such closed or partially closed environments will share exposure to pathogens, such environments may pose a significant infection risk. This problem may be particularly severe in facilities with numerous high numbers of occupants, such as hospitals and schools, especially when such occupants may be exposed to the environment for extended lengths of time.

One conventional approach to this problem is to cycle the air inside such closed or partially closed environments through air treatment systems including filters sufficiently fine to capture pathogens that may be in the air. However, filters may impede air flow in environments where a certain volume of air flow is necessary or desirable. Moreover, conventional filter-only air treatment systems alone may not kill or deactivate pathogens and may grow less effective over their service lives as particulate matter builds up in the filters.

One alternative to the filter-only approach is to treat the air in a room with ultraviolet light to kill or deactivate any pathogens in the air. The intensity of ultraviolet light should be sufficient to kill or deactivate pathogens in a relatively short exposure time, and should be capable of being repeated easily, as additional pathogens may enter the air even after an initial treatment has been performed. But use of unshielded ultraviolet light can pose health hazards to any occupants of a room being treated. Prolonged exposure to ultraviolet light may, for example, cause skin damage, eye damage, and various types of cancer in humans. Additionally, some wavelengths of ultraviolet light may produce ozone, which can also be harmful for occupants. For this reason, an unshielded ultraviolet light source may be unsuitable for treating circulating air in a room currently in use and may be feasible only during times a room is not in use.

The air treatment systems disclosed herein include sources of ultraviolet light to kill or neutralize airborne pathogens in a closed environment or partially closed environment. The ultraviolet light sources are contained within a housing to support the ultraviolet light sources and to prevent emitted ultraviolet light from reaching any occupants in that environment, allowing for long duration or continuous use, even when a room is occupied. Additionally, the air treatment systems disclosed herein are designed to move air rapidly through the housing to ensure that the air within the closed or partially closed environment is cycled multiple times per hour for continuous neutralization of pathogens in the air.

Figure 3:
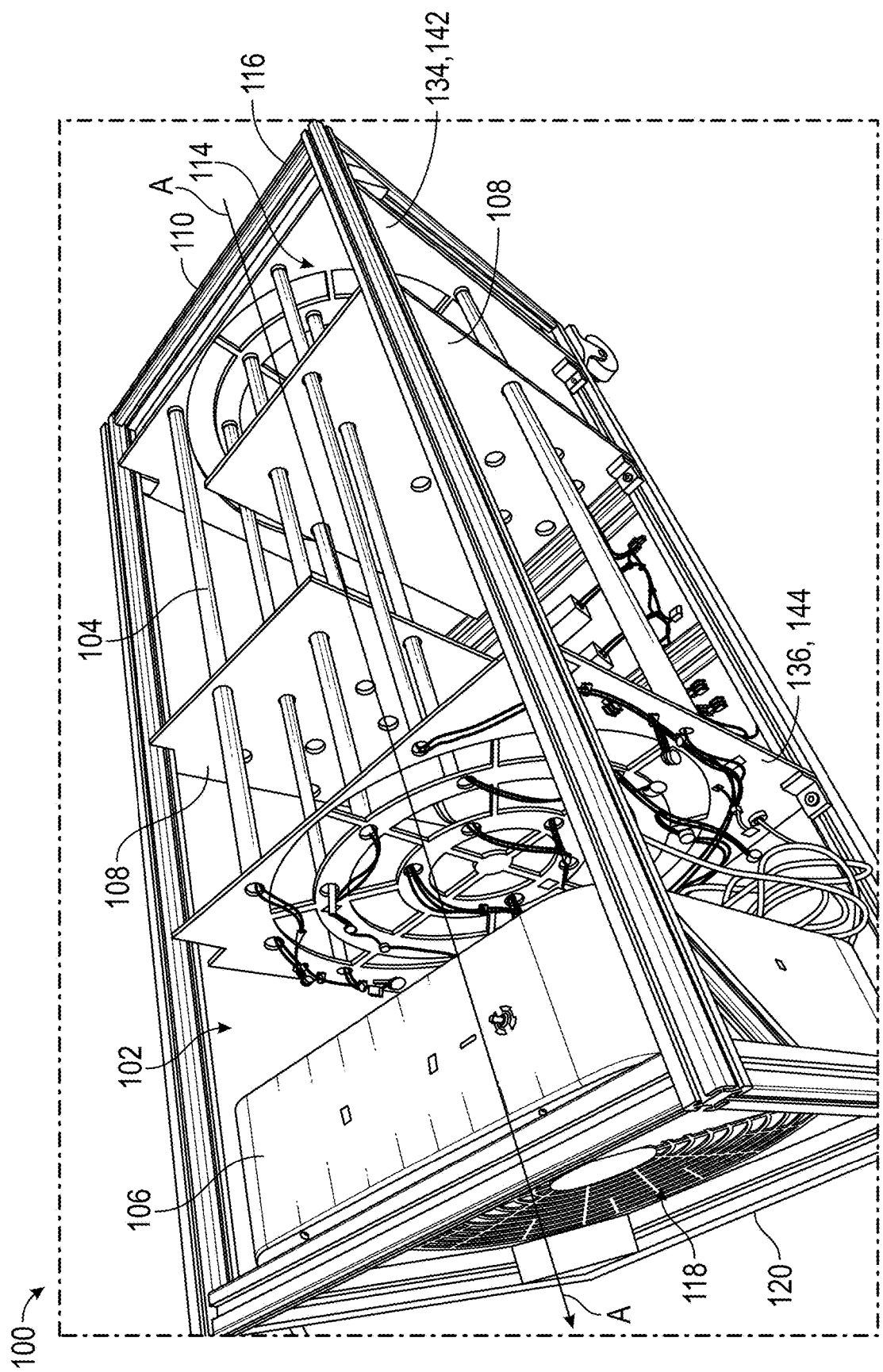
FIG. 3 is a partial perspective view of the air treatment system of FIG. 1 also depicting an air moving system, light sources and wiring installed.

The air treatment systems disclosed herein comprise a housing, an ultraviolet light source, and an air moving device. For example, the air treatment system 100 shown in FIG. 1 can comprise a housing 102. One or more ultraviolet light sources 104 can be disposed within the housing. An air moving device 106, as shown in FIG. 3, can be positioned in or next to an opening of the housing. As also shown in FIG. 3, a forced air direction A indicates the principal direction that air is forced (or drawn) by the air moving device 106. In some examples, the air treatment system 100 can also include one or more interior baffles 108.

Figure 2:
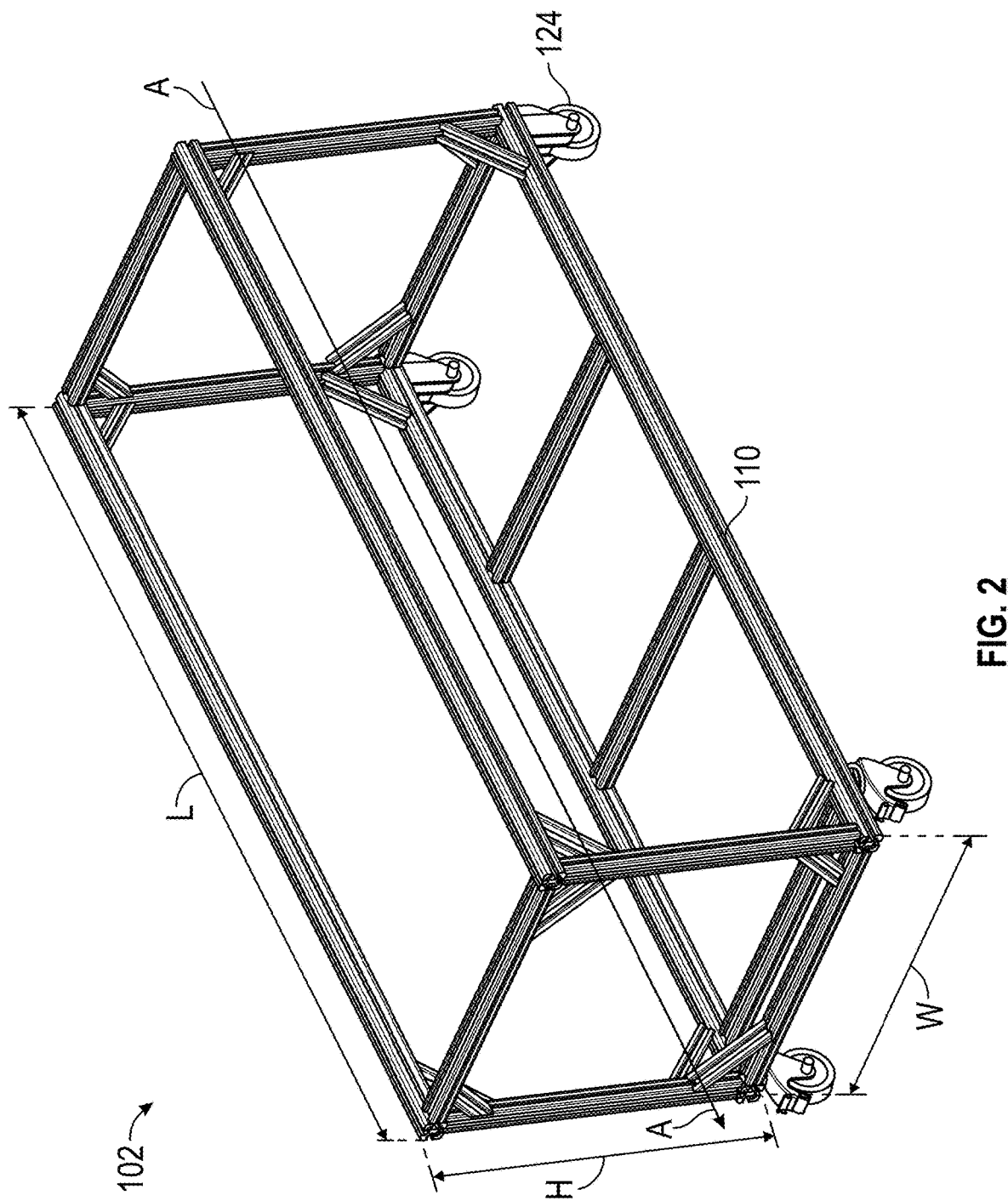
FIG. 2 is a perspective view of the frame of the air treatment system of FIG. 1.

Turning now to FIG. 2, the housing 102 can have a frame 110. In some examples, such as that shown in FIG. 2, the frame 110 has a length L and a rectangular cross section defined by a width W and a height H. As shown in FIG. 2, the forced air direction A can extend generally parallel to the length L of the frame 110. In some examples, as illustrated in FIG. 1, the frame can have an air inlet 114 located at a first end 116 and an air outlet 118 located at a second end 120. It is to be appreciated that in alternative examples, the air inlet 114, the air outlet 118, or both can be located elsewhere on the housing 102, and the forced air direction A may have a different orientation relative to the length L of the housing 102. It is also to be appreciated that in some examples, the housing 102 can comprise more than one air inlet 114 and/or more than one air outlet 118. In other examples, the frame 110 may have a different cross sectional geometry, such as a circular or semi-circular cross section, a triangular cross section, or an irregular cross section.

Figure 6:
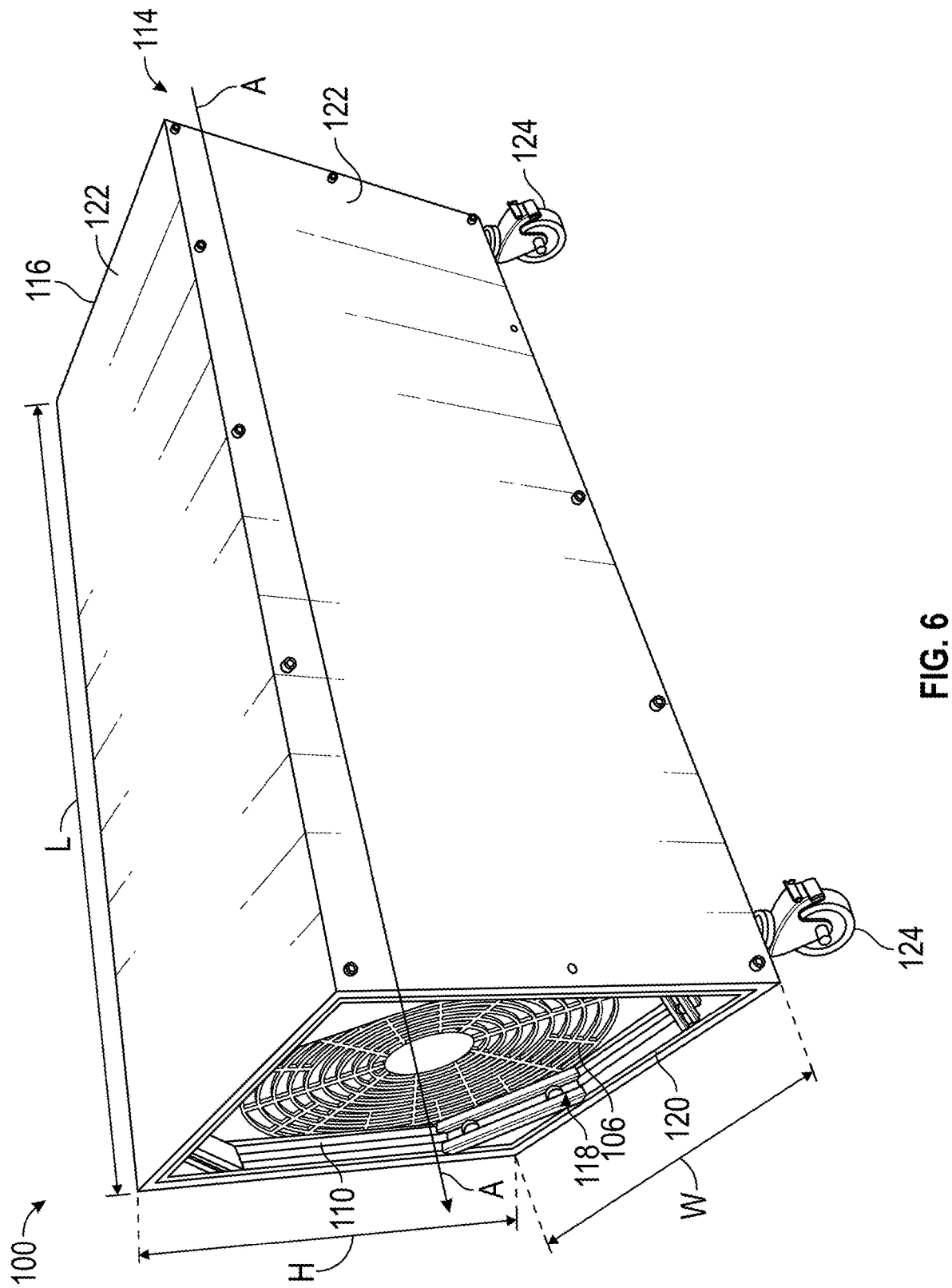
FIG. 6 is a perspective view of the air treatment system of FIG. 3 with all side panels in place.

Turning now to FIG. 6, the air treatment system 100 is shown in a fully assembled state with one or housing panels 122, such as four panels as shown, arranged to enclose include the sides. The housing panels 122 can be positioned along or against one or more exterior surfaces defined by the frame 110. In the example shown in FIG. 6, the housing panels 122 extend along the length L of the housing from the first end 116 to the second end 120, and extend for the full height H or width W of the frame 110.

In some examples, any of the frame 110 or the housing panels 122 can be made of a material that tends to reduce the transmission of ultraviolet light, such as may be emitted by ultraviolet light sources 104. For example, the frame 110 and/or the housing panels may be made out of any of a metal, particularly aluminum or steel, a polymer, or natural materials such as wood. In some examples, the material selected for the housing panels 122 may fully or nearly fully block the emission of ultraviolet light from within the housing 102. In this way, ultraviolet light emitted by ultraviolet light sources 104 can be prevented from exiting the housing 102 and entering the nearby environment in which the air treatment system 100 is operating.

With continued reference to FIG. 6, the air treatment system 100 may in some examples, include one or more casters 124 or other similar device to assist in moving the system when desired. The casters 124 can be attached to elements of the frame 110 or to the housing panels 122, and can be spaced to support the weight of the air treatment system 100 and to permit the air treatment system 100 to be repositioned to any room to be treated by rolling. In the example illustrated in FIG. 6, the air treatment system 100 is shown as having 4 casters, however other examples may have more casters 124, such as 6, 8, 10, or 12 casters 124. It is to be appreciated that in alternative examples, the air treatment system 100 may omit the casters 124 and can be installed immovably or permanently in a room to be treated. It is also to be appreciated that alternative devices may be used to allow for convenient repositioning of the air treatment system 100.

Figure 10:
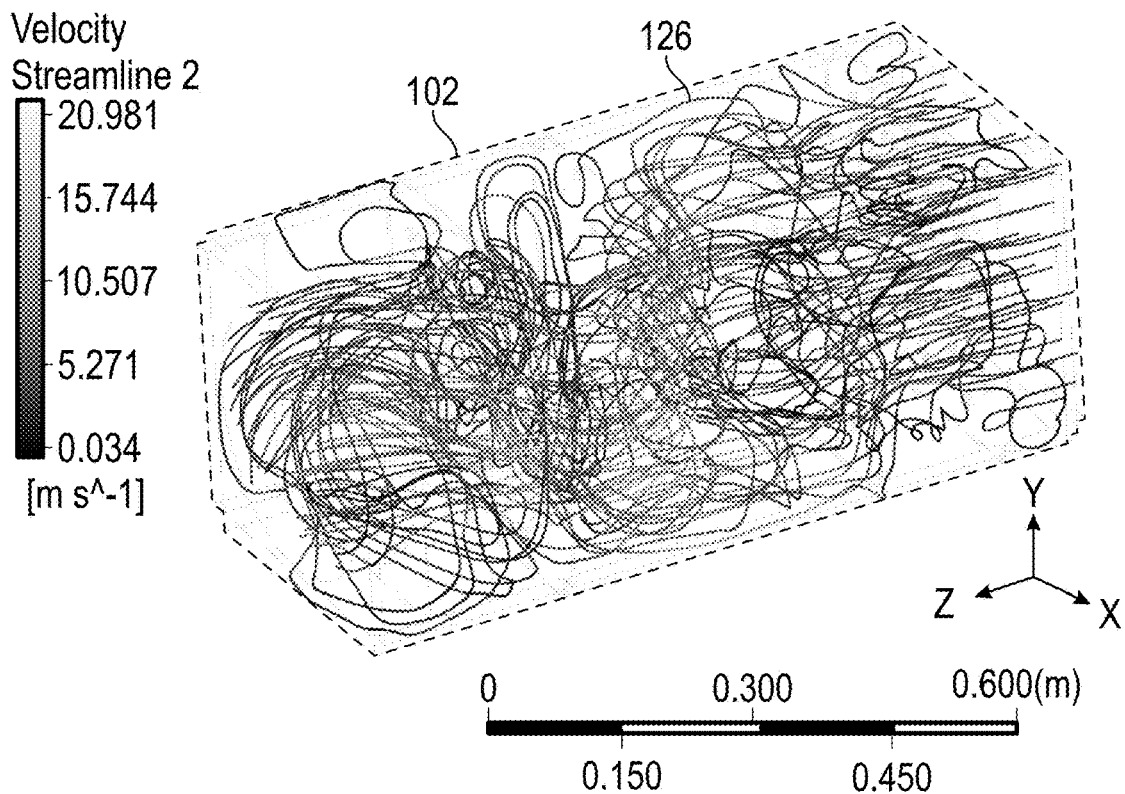
FIG. 10 depicts a three-dimensional computational fluid dynamic model of airflow velocity in an example air treatment system.
Figure 11:
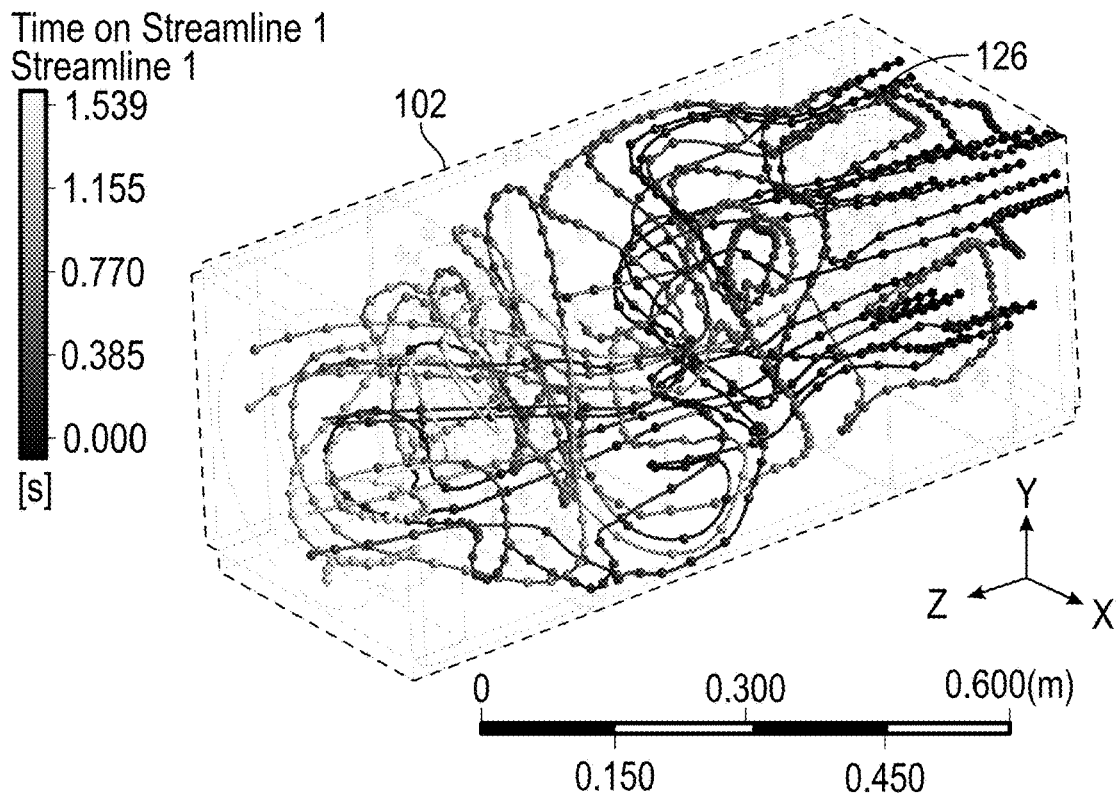
FIG. 11 depicts a three-dimensional computational fluid dynamic model of the time duration air particles spend within an example air treatment system.

Referring again to FIG. 3, the air moving device 106 is configured to generate the airflow through the housing 102 along the forced air direction A, such as the airflow 126 illustrated in FIGS. 10 and 11. The air moving device 106 can be positioned at the air inlet 114 or the air outlet 118 (i.e., at the first end 116 or the second end 120 in the example shown in FIGS. 1 and 3). In examples having the air moving device 106 at the air inlet, the air moving device can draw in air from outside the housing 102 and can push the air through the housing to generate the airflow 126 (this may be described as running the air moving device 106 in a "pushing" mode). In examples having the air moving device 106 at the air outlet, the air moving device can draw in or "pull" air through the air inlet 114 and the housing 102 to generate the airflow 126, expelling it through the air outlet 118 (this may be described as running the air moving device 106 in a "pulling" mode). It is to be appreciated that, while FIG. 3 depicts an example air treatment system 100 having one air moving device 106, in other examples the air treatment system may have more than one air moving device 106, such as two, three, or four air moving devices 106. In examples having more than one air moving device 106, the multiple air moving devices 106 can be positioned at different locations relative to the housing. For instance, one example air treatment system 100 could have a first air moving device 106 at the air inlet 114 and a second air moving device 106 at the air outlet 118.

In examples having the air inlet 114 at the first end 116 and the air outlet 118 at the second end 120 of the housing 102, as illustrated in FIG. 6, the forced air direction A may align generally with the length L of the air treatment system 100, as defined by housing 102. It is to be appreciated, that for systems having the air inlet 114 and/or the air outlet 118 disposed at a location other than the first end 116 and the second end 120 of the of the housing 102, the forced air direction A may, in at least some locations, run transverse to the length L of the air treatment system 100 as defined by the housing 102 and may turn and/or mix within the housing.

With continued reference to FIG. 3, the air moving device 106 can be any device suitable for generating an airflow. In some examples, the air moving device 106 can be, for example, an HVAC blower, a centrifugal blower (sometimes called a "squirrel cage fan"), or other suitable type of air moving device. In other examples, such as the specific illustrated embodiment of FIG. 3, the air moving device can be a conventional box fan.

The air moving device 106 is configured to produce an airflow having a particular flow rate. In some examples, the flow rate of the airflow is between 600 and 2000 cubic feet per minute ("cfm"), such as 600 cfm, 700 cfm, 800 cfm, 900 cfm, 1000 cfm, 1100 cfm, 1200 cfm, 1300 cfm, 1400 cfm, 1500 cfm, 1600 cfm, 1700 cfm, 1800 cfm, 1900 cfm, 2000 cfm or any flow rate in between. In other examples, the flow rate of the airflow may be expressed as a minimum flow rate, for instance at least 600 cfm, at least 700 cfm, at least 800 cfm, at least 900 cfm, at least 1000 cfm, at least 1100 cfm, at least 1200 cfm, at least 1300 cfm, at least 1400 cfm, at least 1500 cfm, at least 1600 cfm, at least 1700 cfm, at least 1800 cfm, or at least 1900 cfm.

Turning now to FIGS. 10 and 11, the airflow 126 moving through the housing 102 may have a velocity that varies along the length L of the housing 102 within a range of velocities. For instance, as illustrated in FIG. 10, the airflow 126 may have an instantaneous velocity that ranges from greater than 0 m/s to less than or equal to 20 m/s along the length L of the housing, such as 2 m/s, 4 m/s, 6 m/s, 8 m/s, 10 m/s, 12 m/s, 14 m/s, 16 m/s, 18 m/s, 20 m/s or any velocity in between. In particular examples, the airflow 126 can pass through the housing 102 with an average velocity ranging from greater than 0.5 m/s to 10 m/s, such as greater than 1 m/s to 10 m/s, greater than 2 m/s to 10 m/s, greater than 3 m/s to 10 m/s, greater than 4 m/s to 10 m/s, greater than 5 m/s to 10 m/s, greater than 6 m/s to 10 m/s, greater than 7 m/s to 10 m/s, greater than 8 m/s to 10 m/s, and greater than 9 m/s to 10 m/s. In one specific example, the airflow 126 can pass through the housing 102 with an average velocity of 0.76 m/s, with a velocity at the midpoint of the housing 102 of 1.43 m/s, and an airflow at the air outlet 118 of 1.48 m/s. In another specific example, illustrated in FIG. 10, the average velocity of the airflow 126 passing through the housing 102 can be 4.62 m/s. It is to be appreciated that the instantaneous and average velocities of the airflow 126 passing through the housing 102 may rely on many variables, including the flow rate of the airflow 126, the cross-sectional area of the housing 102, and any obstructions or baffles included in the housing which may tend to impede or disrupt the airflow 126.

With continued reference to FIGS. 10 and 11, the duration that any portion of airflow 126 or any particles entrained therein remains within the housing 102 is determined by the velocity of the airflow 126. In this way, air moving at a lower velocity may spend longer within the housing 102 of the air treatment system 100 and air moving at a higher velocity may spend less time within the housing 102 of the air treatment system 100. As will be discussed in greater detail below, the time within the housing correlates to the time that any pathogens entrained within the airflow 126 is exposed to the ultraviolet light sources 104. In one example, illustrated in FIG. 11, the average velocity of 4.62 m/s results in an average time of exposure to the ultraviolet light sources 104 of 0.387 seconds. Therefore, it is to be appreciated that both high flow rates and low flow rates may be desirable for various reasons. For example, a high flow rate, such as a flow rate above 1000 cfm may be desirable to allow the air treatment system to treat the air in a room many times per hour. In one particular example, an air treatment system 100 having an airflow 126 of 1000-1700 cfm can change the air in a 30'×30'×11' room (i.e., a 10000 cubic foot room) between 6 and 10 times per hour (sometimes referred to as 6-10 ACH). In environments such as hospitals, where a minimum level of air recirculation is desirable, such high flow rates and corresponding high velocities may be particularly advantageous. Alternatively, lower flow rates of airflow 126 correspond to lower velocities of airflow 126. If the velocity of airflow 126 is lower, then pathogens or pathogen bearing aerosols and droplets entrained in the airflow 126 will spend more time exposed to the level of ultraviolet irradiance within the housing 102, which may in turn allow for higher rates of pathogen deactivation and/or lower allowable levels of ultraviolet irradiance intensity.

Returning now to FIG. 1, the ultraviolet light sources 104 of the air treatment system 100 are typically disposed within the housing 102. In some examples, such as that illustrated in FIG. 1, the ultraviolet light sources 104, can be tubular bulbs extending axially along the length L of the frame housing 102 (i.e., parallel to the forced air direction A). As best shown in FIG. 1, the ultraviolet light sources 104 can have a first end portion 128 and a second end portion 130. The first end portion 128 and the second end portion 130 can further comprise electrical leads 132.

Referring now to FIGS. 1 and 3, the ultraviolet light sources 104 can be attached at the first end portion 128 to a first light fixture array 134 and at the second end portion to a second light fixture array 136. As shown in greater detail in FIG. 4, the first light fixture array 134 and the second light fixture array 136 can also include one or more apertures 138 to permit the one or more tubular ultraviolet light sources 104 to extend through or extend partially through the respective light fixture arrays 134, 136. In some examples, the first light fixture array 134 can be positioned adjacent to the air inlet 114 and the second light fixture array can be positioned adjacent to the air outlet 118. In other examples, the first light fixture array 134 can be positioned adjacent to the air outlet 118 and the second light fixture array 136 can be positioned adjacent the air inlet 114. In yet other examples in which the air inlet 114 and/or the air outlet 118 are positioned away from the first end 116 and the second end 120 of the housing 102, the first light fixture array 134 may be positioned adjacent the first end 116 or the second end 120 of the housing 102, and the second light fixture array 136 may be positioned adjacent to the other end.

Figure 4:
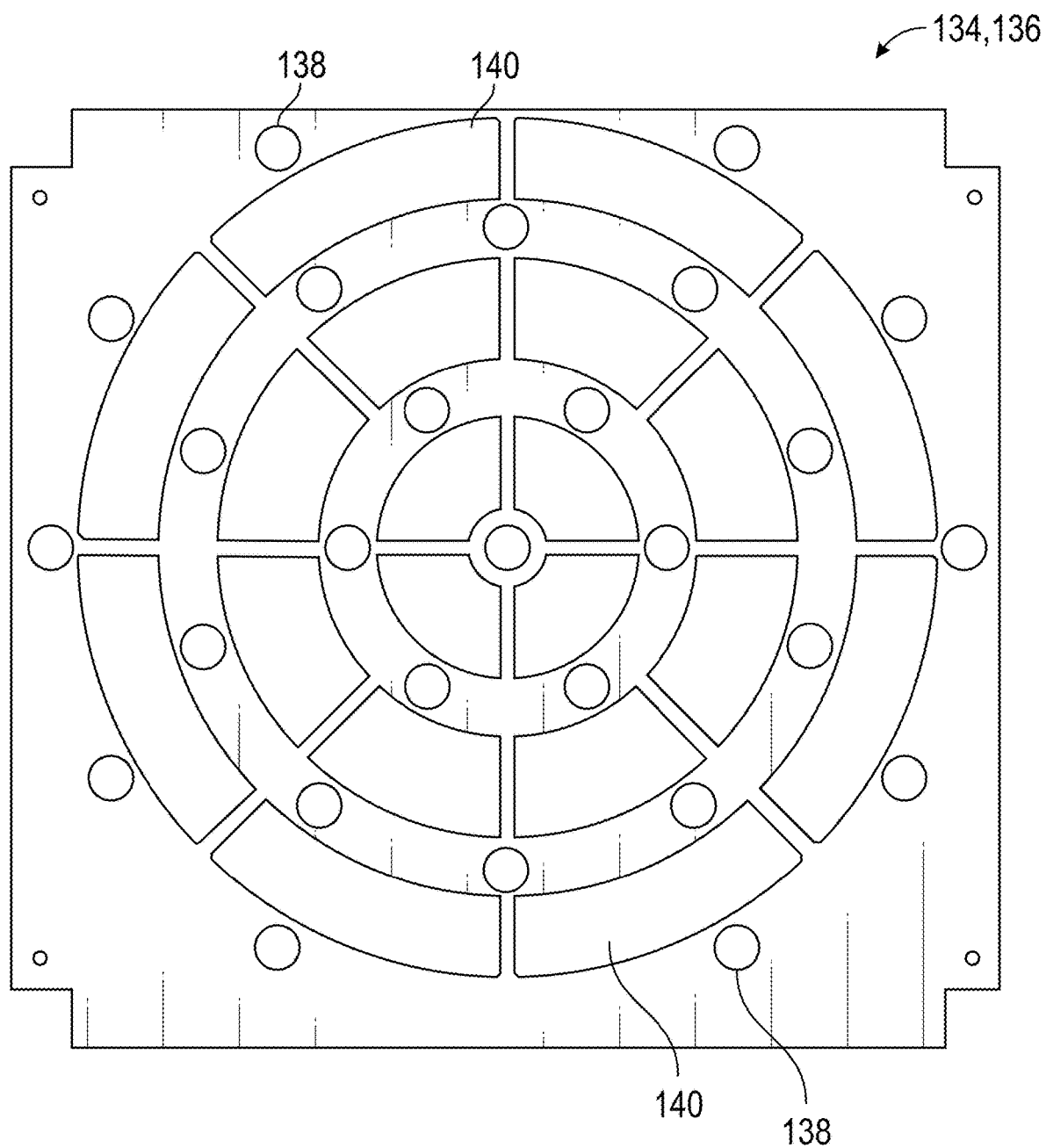
FIG. 4 is an elevation view of a light fixture with air bypass apertures for use in an air treatment system.

Returning to FIGS. 1 and 3, the first light fixture array 134 and the second light fixture array 136 can be plates disposed within the housing 102 perpendicular to, or at another angle transverse to, the forced air direction A. In such examples, best shown in FIG. 4, the first light fixture array 134 and the second light fixture array 136 can also include one or more air passages 140. The air passages 140 can be configured to allow the airflow 126 passing through the air treatment system 100 to partially bypass the light fixture arrays 134, 136, disrupting the airflow 126 and causing or increasing mixing of the airflow 126 within the housing 102 of the air treatment system. In such examples, the first light fixture array 134 and the second light fixture array may further function as a first end baffle 142 and a second end baffle 144. While FIGS. 1, 3, and 4 show the air passages 140 disposed in a pattern of concentric circles around a central point on the light fixture arrays 134, 136, it is to be appreciated that alternative configurations are possible.

While FIGS. 1 and 3 depict an air treatment system 100 having a plurality of tubular ultraviolet light sources 104 that extend along the length of the housing 102, it is to be appreciated that alternative configurations for ultraviolet light sources 104 and their arrangement within the housing 102 are possible. For instance, in an alternative example, the ultraviolet light sources 104 could be ultraviolet LED lights disposed along an internal surface of the housing 102, and light fixture arrays 134, 136, and/or against any interior baffles 108 disposed within the housing 102. In yet another alternative example, the ultraviolet light sources 104 can be circular ultraviolet lamps positioned against an internal surface of the housing 102, and the light fixture arrays 134, 136, and/or against any interior baffles 108 disposed within the housing 102.

Figure 12:
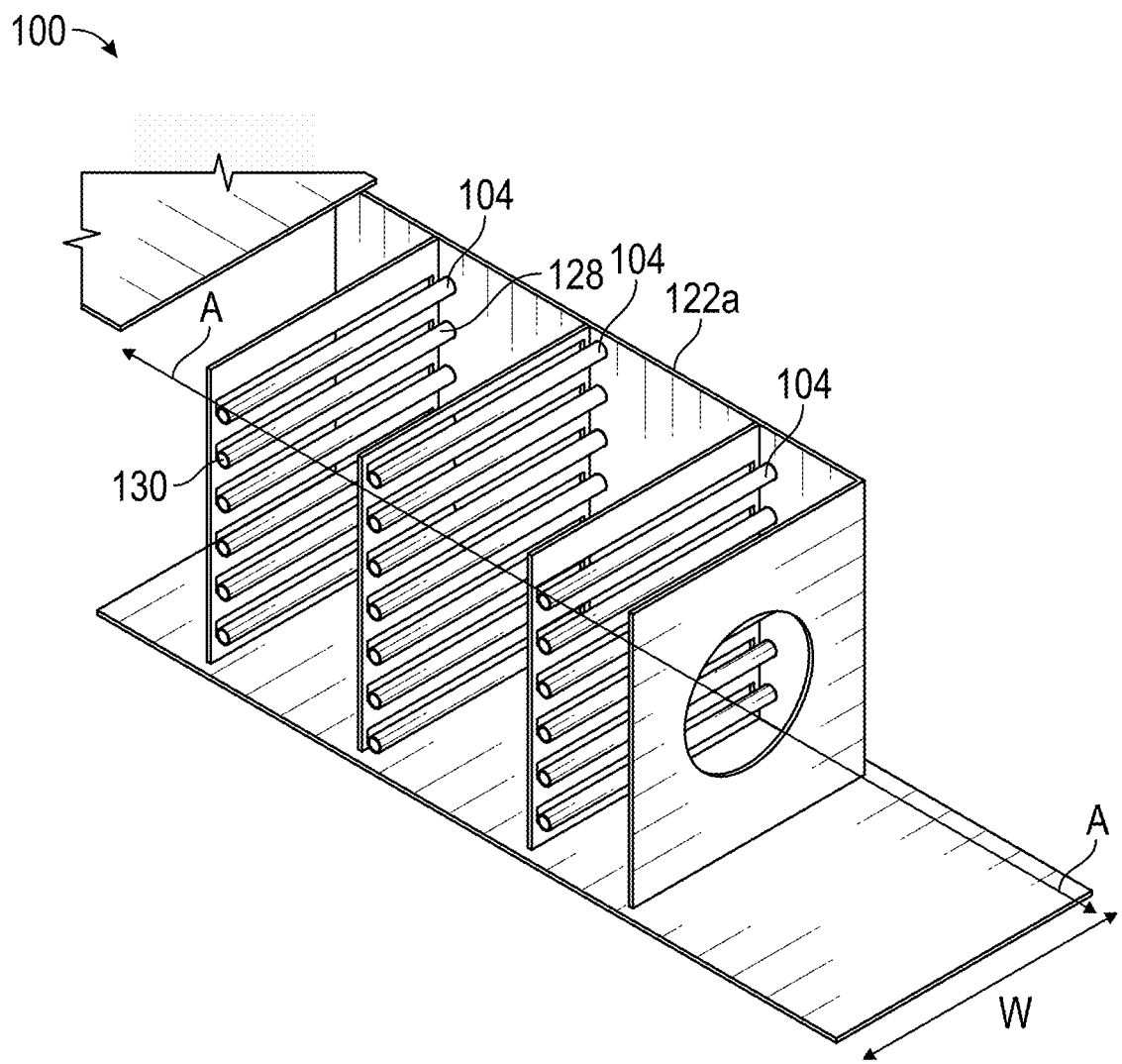
FIG. 12 is a perspective view of an air treatment system according to another example having light sources extending transverse to the forced air direction imparted by the air moving device.
Figure 13:
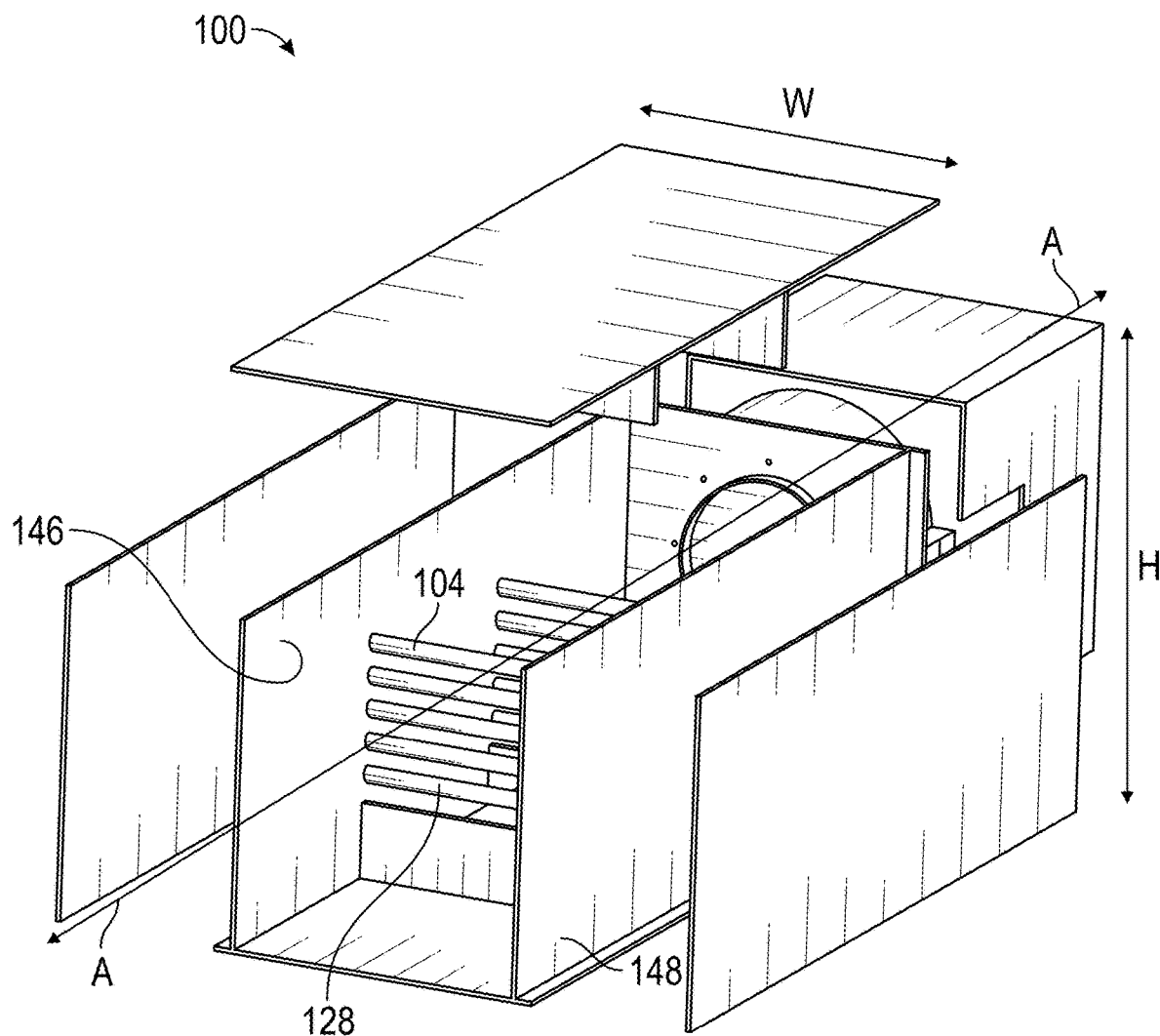
FIG. 13 depicts an air treatment system according to an alternative example having lights transverse to the forced air direction imparted by the air moving device.

In an alternative example, shown in FIGS. 12 and 13, the ultraviolet light sources 104 can be disposed within the housing 102 such that the ultraviolet light sources 104 extend transverse to the forced air direction A (e.g., including parallel to the width W or the height H) of the housing 102. In such examples, the airflow 126 along the forced air direction A can move between and past, rather than along the ultraviolet light sources. As illustrated in FIG. 12, the ultraviolet light sources 104 can be attached at the first end portion 128 to a first housing panel 122a, and at the second end portion 130 to a second housing panel (not shown) and can extend parallel to the width W of the housing 102. Alternatively, as illustrated in FIG. 13, the ultraviolet light sources 104 can be attached at the first end portion 128 to a first interior panel 146 and at the second end portion (not shown) to a second interior panel 148, and can extend parallel to the width W of the housing 102. Although FIGS. 12 and 13 depict the ultraviolet light sources 104 extending parallel to the width W of the housing 102, in alternative examples, the ultraviolet light sources 104 could instead extend parallel to the height H of the housing 102.

The ultraviolet light sources 104 can be configured to emit light with a wavelength ranging from 100 nm to 400 nm (i.e., ultraviolet or UV light). In some particular examples, the light emitted can more specifically have a wavelength ranging 315 nm and 400 nm (UVA light), ranging from 280-315 nm (UVB light), or ranging from 100 nm to 280 nm (UVC light). In one specific example, the ultraviolet light sources 104 emit light with a wavelength of 254 nm. Examples having ultraviolet lights configured to emit light with a wavelength ranging from 100-280 nm (UVC light) may be particularly advantageous, because this wavelength range is the highest-energy wavelength range of ultraviolet light. Additionally, UVC light may produce limited ozone, substantially no ozone, or no ozone. Thus, when ultraviolet light sources 104 emit UVC light, air treatment system 100 can advantageously operate without producing a hazardous level of ozone in environments being treated. Furthermore, higher energy UVC light may allow greater or more rapid deactivation of pathogens passing through the air treatment system 100.

The number of ultraviolet light sources 104 disposed within the housing 102 can be selected based on a number of factors, including the desired intensity of UV light irradiance within the housing while the air treatment system is operating. In some examples, the target UV light irradiance may be at least 1 mJ/cm$^2$, such as 1.5 mJ/cm$^2$ or greater, 2 mJ/cm$^2$ or greater, 2.5 mJ/cm$^2$ or greater, 3 mJ/cm$^2$ or greater, 3.5 mJ/cm$^2$ or greater, 4 mJ/cm$^2$ or greater, 4.5 mJ/cm$^2$ or greater, or 5 mJ/cm$^2$ or greater. In other examples, a target irradiance may be range from 0.5 mJ/cm$^2$ and 4 mJ/cm$^2$, such as 1 mJ/cm$^2$, 1.5 mJ/cm$^2$, 2 mJ/cm$^2$, 2.5 mJ/cm$^2$, 3 mJ/cm$^2$, 3.5 mJ/cm$^2$, and 4 mJ/cm$^2$. It is to be understood that the intensity of the irradiance provided by the ultraviolet light sources 104 may depend on a number of factors, including the number of ultraviolet light sources 104 used in the air treatment system 100, the geometry of the housing 102, and the specific arrangement of the ultraviolet light sources 104. For example, intensity may be increased by including more powerful or numerous ultraviolet light sources 104, by reducing the spacing between the ultraviolet light sources 104, and/or by reducing the cross-sectional area of the housing 102 to reduce the maximum distance from any ultraviolet light source 104 within the housing 102. As will be discussed in greater detail below, the various example air treatment systems herein may have ultraviolet light sources 104 configured such that the intensity of emitted ultraviolet light can deactivate pathogens entrained in the airflow 126, particularly viruses such as the Sars-Cov-2 virus.

Returning now to FIG. 1, the air treatment system 100 can also include one or more interior baffles 108 disposed within the housing 102. The interior baffles 108 may extend transverse to the primary direction of the airflow 126 (i.e., transverse to the forced air direction A within the housing 102) across some or all of the cross-sectional area of the housing 102, such that the airflow 126 impinges on the one or more interior baffles 108. Interior baffles 108 can be configured to obstruct or partially obstruct the airflow 126, thereby disrupting the linear flow of air within the housing 102, increasing turbulence, and improving the mixing of air within the housing 102.

Figure 5:
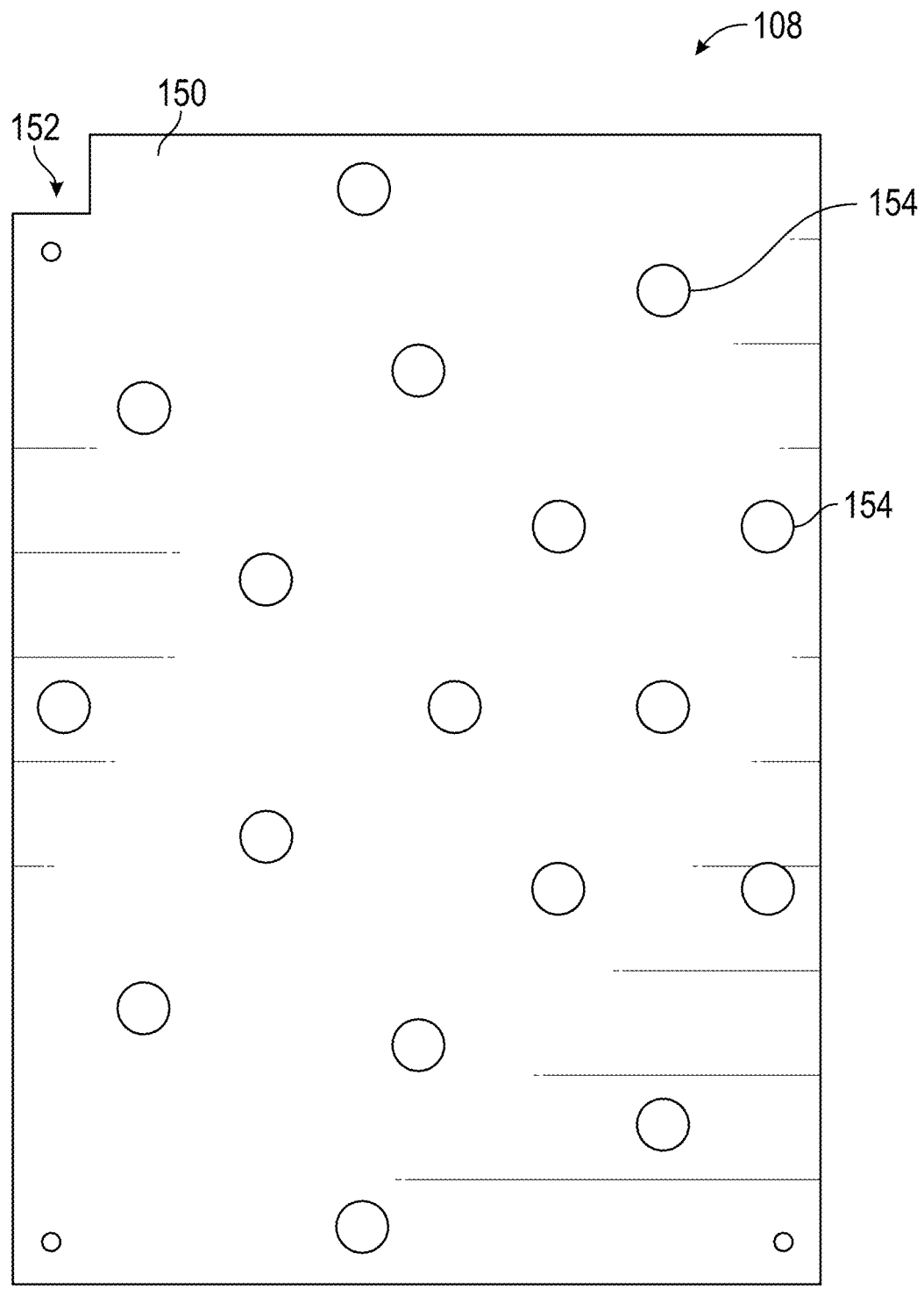
FIG. 5 is an elevation view of a baffle with apertures therein for use in an air treatment system.

As best illustrated in FIG. 5, the interior baffles 108 can comprise a plate 150 with one or more apertures 154 (or openings 154). The apertures 154 may have various functions. For instance, in some examples the apertures 154 can be configured to receive the ultraviolet light sources 104, allowing the ultraviolet light sources 104 to extend through the interior baffles 108, as illustrated in FIGS. 1 and 3. In other examples, as shown in FIG. 3, some of the apertures 154 can be left unoccupied or open. In such examples, some of the unoccupied or open apertures 154 can provide passages for the airflow 126 to pass through the interior baffle 108, rather than around the interior baffle 108, increasing mixing in the airflow 126. The plate 150 can also have one or more notches 152 or other similar features to adapt the plate 150 for mounting within the housing 102.

As shown in FIGS. 1 and 3, the one or more interior baffles 108 can be disposed between the first light fixture array 134 and the second light fixture array 136. In example air treatment systems 100 in which the first light fixture array 134 and the second light fixture array 136 act as baffles, the air treatment system can include three or more baffles within the housing 102 in total. For instance, the example air treatment system illustrated in FIGS. 1 and 3 may comprise a first end baffle 142 and a second end baffle 144 in addition to two interior baffles 108 for a total of four baffles. It is to be understood that while FIGS. 1 and 3 show an air treatment system 100 having two interior baffles 108 disposed between the first light fixture array 134 and the second light fixture array 136, a different number of interior baffles 108, such as one, three, four, or five interior baffles 108 could be included instead.

Taken together, the end baffles 142, 144 (i.e., the light fixture arrays 134, 136) and the one or more interior baffles 108 can form a tortuous path through the housing 102 and can increase the mixing of the airflow 126 within the housing 102, as illustrated in FIGS. 11 and 12. The tortuous path through the housing can force the airflow 126 to depart from a linear flow, as illustrated in FIGS. 10 and 11, from the air inlet 114 to the air outlet 118. This departure from a linear path effectively multiplies the total distance any pathogen or pathogen-containing aerosol entrained in the airflow 126 travels from the air inlet 114 to the air outlet 118, and consequently the time for which that pathogen or pathogen-containing aerosol may be exposed to the ultraviolet light from ultraviolet light sources 104. As previously discussed, a longer exposure time to the ultraviolet light emitted by ultraviolet light sources 104 may cause a greater fraction of the pathogens in the airflow 126 to become deactivated at any level of ultraviolet light intensity. Additionally, the increased mixing of the airflow 126 can improve the uniformity of exposure of pathogens or pathogen-containing aerosols entrained in the airflow 126 to the ultraviolet light emitted by ultraviolet light sources 104.

In some examples, the arrangement of the first end baffle 142 and the second end baffle 144 and the interior baffles 108 can be configured to cause a minimal obstruction of airflow through the air treatment system 100. In some examples, the pressure drop caused by resistance to airflow between the air inlet 114 and the air outlet 118 of the air treatment system can be less than 1.0 inch of water column ("in. W.C."), such as 0.95 in. W.C or less, 0.9 in. W.C or less, 0.85 in. W.C or less 0.8 W.C. or less, or 0.75 in. W.C or less. A lower pressure drop between the air inlet 114 and the air outlet 118 can be advantageous, because an air treatment system 100 with a lower air pressure drop is able to treat greater air throughput with less work from the air moving device 106.

In some examples, the air treatment system 100 can also include one or more air filters 98a and/or 98b, as shown schematically in FIG. 1. The air filters 98a, 98b can be disposed at either the air inlet 114 or the air outlet 118 of the air treatment system 100, and can be configured to filter particulate matter out of the airflow 126 either prior to or after entering the housing 102. It is to be appreciated that the air filters 98a, 98b can thus be positioned either on the same end of the housing 12 as the air moving device 106 or on the opposite end of the housing 102 (i.e., in some examples, the air filter and the air moving device 106 can be located both at the first end 116 of the housing 102, both at the second end 120 of the housing 102, or one each at the first end 116 and the second end 120 of the housing).

In examples having the air filter 98a located at the air inlet 114 of the air treatment system 100, the air filter 98a can advantageously remove particulate matter from the airflow 126 before it can enter the housing 102. Particulate matter in the airflow 126 that enters the housing 102 can be deposited or settle on the ultraviolet light sources 104. Over time, the accumulation of particulate matter on the ultraviolet light sources 104 can partially block the ultraviolet light sources 104 and decrease the intensity of light emitted within the housing. It is therefore desirable to remove this particulate matter from the airflow 126 before entry into the housing 102.

The air filters 98a, 98b can, in some examples, be of the same type(s) as conventional furnace filters. Many kinds of such filters may be suitable for use in the air treatment system 100, such as fiberglass filters, polyester filters, electrostatic filters, pleated filters, or HEPA filters. It is to be appreciated that a variety of filters may be appropriate for various reasons. For example, filters with the ability to capture very fine particulate matter at high rates of capture may extend the lifetime of the ultraviolet light sources 104 by more fully removing particulate matter from the airflow 126, whereas more permeable filters may be suitable for minimizing any obstruction to airflow 126.

In other examples, the air filter 98a or 98b can be a roughing filter. A roughing filter can be positioned near the air inlet 114, and can be configured to filter out coarse debris in the air with a minimal detrimental effect on the airflow into the housing 102 of the air treatment system 100. In some examples, the roughing filter 98a, 98b may be combined with a furnace filter such as those previously discussed to provide for at least one filter configured for coarse debris removal and at least one filter 98a, 98b configured to remove fine particulate matter from the airflow 126.

Figure 8:
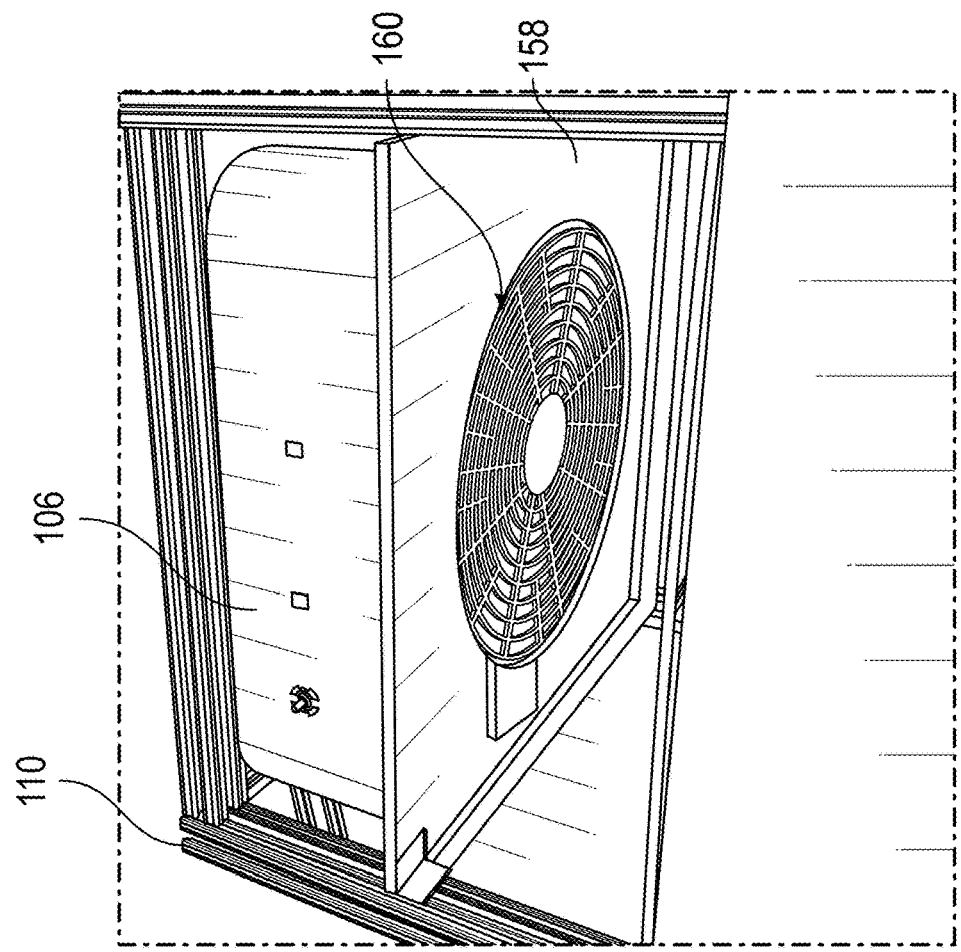
FIG. 8 is an elevation view of the air moving system shown in FIG. 3 mounted adjacent to an orifice plate.
Figure 7:
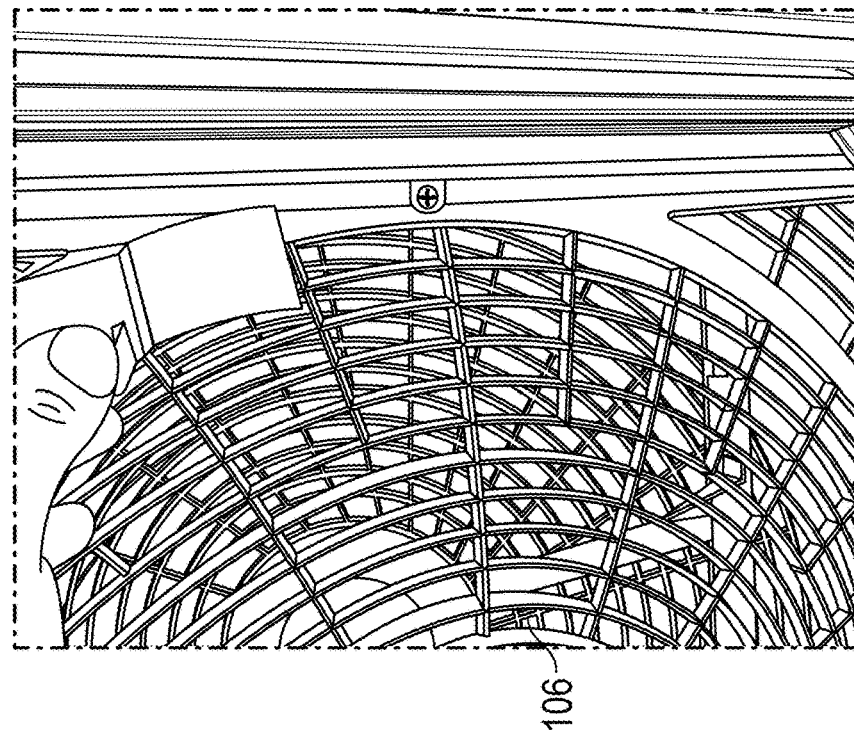
FIG. 7 is a partial perspective view of an air moving device according to one embodiment mounted in an air treatment system.
Figure 9:
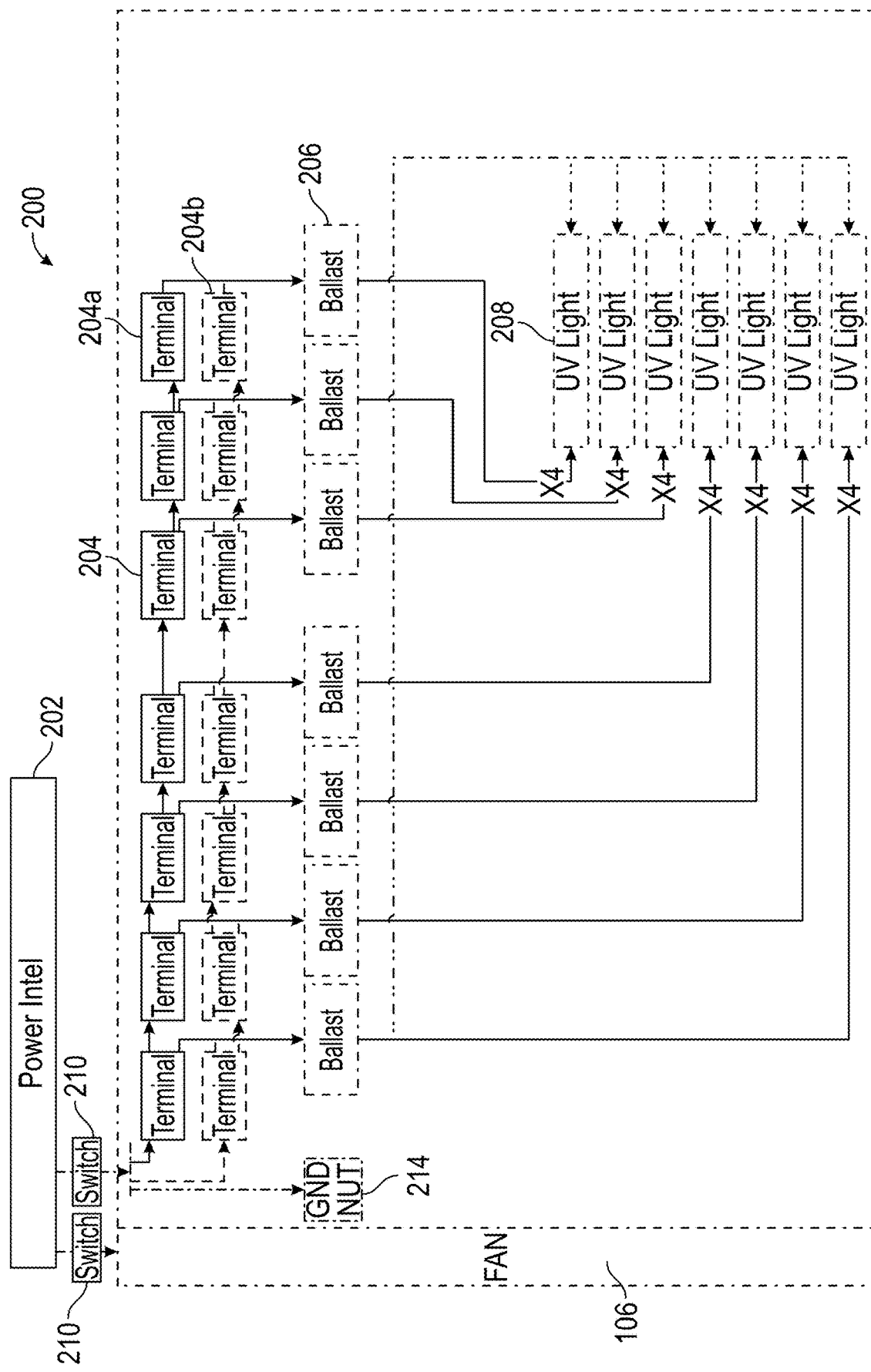
FIG. 9 depicts a general electrical schematic for an example air treatment system.

Turning now to FIG. 8, the air treatment system 100 can also include an orifice plate 158. The orifice plate 158 can be located at the air inlet 114 or the air outlet 118, adjacent to the air moving device 106, and can be configured to prevent air backflow around the air moving device 106. Significant air backflow can severely impede the volume of airflow 126 through the housing of the air treatment system. The orifice plate 158 can further comprise an airflow aperture 160 to permit passage of air through the air moving device 106. The backflow orifice seal can be made from any easily formed material capable of sealing off or occluding gaps between the air moving device 106 and the frame 110 around the air inlet 114 and/or the air outlet 118, such as plywood, aluminum, steel, elastomeric materials, or polymers.

Also disclosed herein is an exemplary electrical assembly 200 that can be used in conjunction with air treatment systems such as air treatment system 100 to run the ultraviolet light sources 104 and the air moving device 106 previously discussed. Turning now to FIG. 10, electrical assembly can comprise a power connection 202, one or more electrical terminals 204, one or more electrical ballasts 206, and a plurality of UV lights 208. In some examples, the electrical assembly 200 can also include one or more switches 210.

As shown in FIG. 10, the power connection 202 can connect to an external power source (i.e., an electrical outlet providing AC power) and route power to the electrical terminals 204, which can further comprise one or more first electrical terminals 204a and one or more second electrical terminals 204b. In some examples, such as that illustrated in FIG. 10, the number of first electrical terminals 204a and second electrical terminals 204b may be equal. The first electrical terminals 204a and second electrical terminals 204b can be connected to one or more electrical ballasts 206.

The electrical assembly 200 can also include a plurality of UV lights 208. As shown in FIG. 10, the plurality of UV lights 208 can be ballasted with the electrical ballasts 206. The electrical ballasts 206 can be configured to ignite the UV lights 208 with an initial discharge arc. In some specific examples, electrical ballasts 206, and may prove advantageous for their relatively high efficiency, and suitability for applications in which the UV lights 208 are not cycled on and off frequently. It is to be appreciated that other electrical ballast types may be suitable for use with the electrical assembly 200.

As shown in FIG. 10, the number of electrical ballasts 206 may be selected according to the number of UV lights 208 used. In some examples, each electrical ballast 206 can be attached to more than 1 UV light 208. For example, as illustrated in FIG. 10, each electrical ballast 206 can be connected to 4 UV lights 208. It is to be appreciated that each electrical ballast 206 can be connected to a greater or smaller number of UV lights 208, such as 1, 2, 3, 5, 6, 7, or 8 UV lights 208.

In some examples, the power connection 202 can also supply power to an air moving device, such as the air moving device 106, 212.

The electrical assembly 200 can also include an electrical ground 214. The electrical ground 214 is connected to the power connection 202, the one or more first electrical terminals 204a, and the one or more second electrical terminals 204b.

Air treatment systems disclosed herein, such as the air treatment system 100, can be employed to disinfect air being circulated through a closed or partially closed environment such as a room or building. The various examples of air treatment systems described herein are capable of producing at least a 99% deactivation of pathogens, such as entrained virus particles or aerosols that contain virus particles. Air treatment systems according to some examples disclosed herein are capable of circulating the air in a 10000 cubic foot room at a rate of between 6 and 10 changes per hour, with at least a 99% deactivation of pathogens per change. According to another example disclosed herein, the air treatment systems are capable of circulating the air in a 900 square foot room at a rate of between 6 and 10 changes per hour, with at least a 99% deactivation of pathogens per change. The various examples of air treatment systems disclosed herein thereby meet the demand for improvements to air treatment systems that deactivate virus-containing droplets/aerosols, such as droplets and aerosols containing the SARS-COV-2 virus.

Specific Examples

Disclosed herein are various specific experimental examples of air treatment systems according to the present disclosure. The representative room size chosen for this experimental design was 10,000 cubic feet (30'×30'×11'). A goal of 6-10 air changes per hour (ACH) was chosen. Based on this room size and the ACH goal, a flowrate of 1000-1700 cfm was determined to be necessary to provide an adequate level of protection for a room. A level of UV-C irradiance (254 nm) to produce at least 2 log (99%) deactivation of the SARS-COV-2 virus was desired. Using this target, a design including 27 bulbs, rated at 30 W per bulb, were selected to provide an estimated 49 mJ/cm$^2$ for 1500 cfm of air flowing through a 24"×24" duct. The estimation was computed according to an equation assuming evenly distributed intensity across the cross-section for the full length of the chamber, and a constant airflow.

Example 1: UV-C Air Decontamination System Design

A prototype was designed and built to test the effectiveness of the air treatment system design, as shown in FIGS. 1-3. To facilitate quick fabrication for prototype testing, 80/20 aluminum bars, aluminum panels, 36" UV light tubes, and 3D printed light array panels were used to fabricate the light box. The prototype modeling assumed 1500 cfm of air flowing through a housing with a 24"×24" cross section.

The unit was designed to have a large inlet area with a dust removal filter at the inlet. An array of 27 bulbs, rated at 30 W per bulb, arranged parallel to the direction of flow provide the necessary light intensity to deactivate the virus. Baffles were placed inside the housing design to increase air mixing residence time in the UV irradiation zone, as shown in FIG. 1. A box fan with a theoretical maximum flow rate of 2060 cfm was provided in the prototype design to pull air through the system, as illustrated in FIG. 3. Several CFD analyses were used to optimize airflow through the system during the design phase.

Example 2: Computational Fluid Dynamics (CFD) Analysis

CFD simulations were run on several designs to improve the airflow characteristics prior to creating the final design as shown in this document. Simulations were run at a flowrate of 2060 cfm as that is the maximum flowrate of the box fan used in the prototype design, and results are shown in FIGS. 11 and 12.

FIG. 11 shows the streamline profile for the air treatment system. This design shows several improvements from earlier iterations, namely a fairly even velocity profile with a high degree of mixing and no very high velocity paths that decrease viral deactivation efficiency. This design also has a lower pressure drop compared to previous designs, 0.89 in W.C.

FIG. 10 shows representative particle paths through the system according to the CFD analysis conducted. The average velocity of the air through the unit was 4.62 m/s. The average path length was 1.785 m. The calculated average time of exposure to UV of a particle passing through the air treatment system was determined to be 0.387 s, according to these models.

Example 3: Mechanical Prototype

Once the conceptual design of the system was optimized for airflow, the final prototype design was produced. The frame was constructed from 80/20 extruded aluminum. The frame was 58 inches long by 25 inches wide by approximately 29 inches from the top of the housing to the bottom of the casters, as best shown in FIG. 2. The light array baffles and panels were 3D printed in ABS plastic and secured into the Aluminum frame using L-brackets to the frame, as shown in FIGS. 1 and 3. Aluminum panels were used to enclose the frame's sides, top, and bottom, as best shown in FIG. 6.

FIG. 1 shows the completed system with the top and one side removed to allow interior viewing. 3D light array panels and baffles are secured to the 80/20 bars. The light array panels securely hold the bulbs in the correct locations. The baffles were designed to increase air mixing within the UV light to improve uniformity of UV light exposure of entrained pathogens in the airflow. The baffles were expected to create a slightly larger pressure drop across the system, decreasing the system flow rate, but improve air mixing and purification efficiency.

Electrically, the bulbs were installed in the bulb array panels, the ballasts were secured to the bottom panels, and the box fan was installed. A consumer grade furnace filter was placed at the air inlet of the housing to filter out dust and other particulates that could settle on the bulbs and decrease light intensity over time. A consumer grade box fan was placed at the outlet of the box and the airflow was pulled through the system rather than pushed.

The main maintenance items were identified to be the roughing filter and the lightbulbs. Initial analysis indicated that the filters would need to be replaced once every 30-90 days depending on the frequency of operation and the environmental conditions. The rated life of the bulbs was 8000 hours. Assuming 8 hours of operation a day for 5 days a week, the bulbs were estimated to require replacement once every 4 years. Future design iterations may include a system to notify the operator of bulb failure and filter/bulb life, and studies to determine the decrease in light output of the bulbs as they age are recommended.

Example 4: Electrical Design

The large number of UV light tubes (27) and the limited space for the ballasts, drove the requirement that, in the example prototype, each ballast serve multiple tubes. The UV lights used in this prototype were G30T8 (T8 type, 30 W) 2 pin bulbs having an elongated tubular shape. F30T8 ballasts were selected for compatibility with these UV bulbs. Seven F30T8 Instant Start 4 bulb ballasts were required to support the 27 bulbs. Bi-pin instant start sockets were needed to interface between the ballast and bulbs. Kulka 543 medium bi-pin lamp holders were chosen for their low profile and minimalistic design. Due to the high intensity light in the housing, components required careful selection to prevent degradation of the electrical components over time that could cause electrical safety hazards.

The power draw of the system comprises air moving device and the light sources, i.e., the fan and the light bulbs in this example. The entire system had a power draw of approximately 9 amps, meaning caution was required when determining circuit load, but that a dedicated circuit was not required. This indicated that the design as prototyped would be suitable for use in a variety of room types without the need to provide dedicated electrical circuitry. NRTL components were used for the fan, ballasts, and connectors. The electrical block diagram of FIG. 10, which is described above, provides additional details.

Electrical assembly illustrated several possible mechanical improvements that could improve future designs. First, care should be taken during the mechanical design phase to allow for wiring paths that do not interfere with airflow. A unit with a false bottom and the use of wire looms could also provide additional UV protection to the wiring over the life of the machine. It was also noted that providing access the UV light tubes on one side of the system, such as for maintenance, alleviates the need to disassemble the entire system. Mechanical changes in later designs could create a more easily maintained unit. Due to the spring force applied by the sockets, there was significant deflection in the light array plate. A threaded rod was used in the prototype in order to reduce the deflection, but in future iterations, making these plates out of aluminum in could remove this issue. Choosing a springless socket could also reduce deflection problems in future designs.

Example 5: Prototype Testing

After completion of the mechanical and electrical assembly, the prototype was tested. During testing it was discovered that there were issues with air backflow through the corners of the box fan so that no air was being drawn through the system, as best shown in FIG. 7. A plywood orifice plate, as best shown in FIG. 8, was created to minimize air that could reduce backflow.

An anemometer was used to measure the velocity of the air at various locations throughout the unit. Twelve measurement points were taken at each of the air inlet face and air outlet face of the housing. Eight measurement points were taken at the first interior baffle. Five measurement points were taken at a midpoint between the interior baffles. Six measurement points were taken at the orifice plate. Selected results of the airflow measurement are shown in Table 1 below.

TABLE 1

Airflow Measurements

| | Inlet | Baffle Midpoint | Circular Orifice |
|---|---|---|---|
| Average Velocity (m/s) | 0.76 | 1.43 | 1.48 |
| Flowrate (CFM) | 600 | 578 | 457 |
| Dwell Times | 1.2 | 0.64 | 0.62 |

UV-C intensity was measured with a directional UV-C radiometer (SolarMeter 8.0-RP). Some readings in the initial testing exceeded the maximum reading on the radiometer, so two layers of adhesive plastic film were applied to radiometer which reduced the reading by an estimated 58%. The intensity was measured at the inlet bulb array plate, at the first baffle facing the entrance, at the first baffle facing the exit, and at several locations on the floor. Results of the intensity measurements are shown in Table 2.

TABLE 2

| | UV Intensity and Dosage | | | | | | | |
|---|---|---|---|---|---|---|---|---|
| | First Light Fixture | | First Interior Baffle Inlet Side | | First Interior Baffle Outlet Side | | Housing Floor | |
| | Raw | Actual | Raw | Actual | Raw | Actual | Raw | Actual |
| Average Intensity ($\mu W/cm^2$) | 407 | 702 | 200 | 344 | 452 | 778 | 1431 | 2468 |
| Dosage ($\mu W/cm^2$) | — | 844 | — | 267 | — | 350 | — | 2965 |

Based on results of the prototype testing, it was determined that improvements to the design could be made by using an air movement system with a higher capacity, such as an HVAC blower. It is also believed that measurements of UV light intensity were impaired by the directional nature of the radiometer causing measurements to be taken at a 90° angular offset from the direction of maximum intensity. It is further believed that measurements along the floor of the housing are the most accurate gathered. Despite the difficulties in measuring UV light intensity, measurements taken at the housing floor, which have a maximum average distance from the UV bulbs, show that the UV light was of sufficient intensity to achieve a 2 log (99%) deactivation of entrained pathogens, such as the SARS-COV-2 virus.

Additional Examples of Disclosed Technology

In view of the above-described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. An air treatment system, comprising a housing having an air inlet and an air outlet, an array of ultraviolet light sources disposed within the housing between the air inlet and the air outlet and configured to provide an irradiance dosage of at least 1.5 mJ/cm², an air moving device arranged to generate a forced airflow from the air inlet to the air outlet and past the array of ultraviolet light sources, wherein the forced airflow is at least 1000 cubic feet per minute, and wherein the array of ultraviolet light sources is configured to deactivate virus particles in the forced airflow.

Example 2. The air treatment system any example herein, particularly example 1, wherein the array of ultraviolet light sources produces ultraviolet light with wavelengths ranging from 100 nm to 280 nm.

Example 3. The air treatment system of any example herein, particularly example 1, wherein the housing has a first end and a second end, and wherein the air moving device is positioned at the first end or the second end.

Example 4. The air treatment system of any example herein, particularly example 3, wherein the housing comprises at least one side member configured to reduce transmission of UV light produced within the housing from passing through the side member.

Example 5. The air treatment system of any example herein, particularly example 1, further comprising at least one baffle disposed between the air inlet and the air outlet, the baffle having a plate-like shape and being positioned to extend transverse to a forced air direction such that at least a portion of the forced airflow impinges on the baffle to cause turbulence and increased mixing of the forced airflow in areas upstream and downstream of the baffle.

Example 6. The air treatment system of any example herein, particularly example 5, wherein the baffle comprises first openings shaped to receive at least some of the ultraviolet light sources and second openings shaped to allow the forced airflow to pass through the baffle.

Example 7. The air treatment system of any example herein, particularly example 5, wherein the at least one baffle is a first baffle, further comprising at least a second baffle disposed between the first baffle and the air outlet, the second baffle having a plate-like shape and being positioned to extend transverse to the forced air direction such that at least a portion of the forced airflow impinges on the second baffle to cause turbulence and increased mixing of the forced airflow.

Example 8. The air treatment system of any example herein, particularly example 7, wherein the ultraviolet light sources are disposed between the first baffle and the second baffle in respective first and second lamp holders mounted on the first and second baffles.

Example 9. The air treatment system of any example herein, particularly example 7, wherein the first baffle and the second baffle each comprise first openings shaped to receive at least some of the ultraviolet light sources and second openings shaped to allow the forced airflow to pass therethrough.

Example 10. The air treatment system of any example herein, particularly example 7, further comprising at least a third baffle disposed between the first baffle and the second baffle that extends laterally from a first wall of the housing to partially obstruct a cross section of the housing to define a blocked area and an open area.

Example 11. The air treatment system of any example herein, particularly example 10, further comprising a fourth baffle disposed between the third baffle and the second baffle, that extends laterally from a second wall of the housing opposite the first wall to partially obstruct the cross section of the housing to define a blocked area and an open area.

Example 12. The air treatment system of any example herein, particularly example 1, wherein the ultraviolet light sources have an elongate shape and are positioned to extend lengthwise between the air inlet and air outlet, the ultraviolet light sources being laterally spaced apart from each other in a pre-determined pattern.

Example 13. The air treatment system of any example herein, particularly example 12, wherein the pre-determined pattern is generally circular centered around a centerline of an open area defined by the housing.

Example 14. The air treatment system of any example herein, particularly example 1, further comprising a first panel positioned adjacent to the air inlet and a second panel positioned adjacent to the air outlet, and wherein the first panel and the second panel comprise one or more light mounting locations and airflow openings arranged in a generally circular pattern between the light source mounting locations.

Example 15. The air treatment system of any example herein, particularly example 1, wherein an average velocity of the forced airflow through the housing is less than 5 m/s.

Example 16. The air treatment system of any example herein, particularly example 1, wherein a virus particle in the forced airflow is exposed to the irradiance dosage for at least 0.3 seconds.

Example 17. The air treatment system of any example herein, particularly example 1, further comprising a filter disposed adjacent the air inlet or the air outlet or between the air inlet and air outlet, wherein the filter removes particulates from the forced airflow to reduce an amount of particulates that settles on the ultraviolet light sources.

Example 18. The air treatment system of any example herein, particularly example 17, wherein the air treatment system further comprises a roughing filter configured to filter out particulates ranging from 3 microns to 10 microns in size from the air entering the air inlet.

Example 19. The air treatment system of any example herein, particularly example 1, wherein the air moving device comprises an HVAC blower.

Example 20. The air treatment system of any example herein, particularly example 1, wherein a pressure drop from the air inlet to the air outlet is 1.0 inches Water Column when a flow rate through the housing is 1000 cubic feet per minute or greater.

Example 21. The air treatment system of any example herein, particularly example 1, wherein the air moving device is further comprises a sealing plate configured to prevent a backflow from the air outlet towards the air inlet.

Example 22. The air treatment system of any example herein, particularly example 21, wherein the sealing plate is positioned adjacent the air inlet, and has a circular opening sized to guide the forced airflow through the air moving device.

Example 23. An ultraviolet light air purifier comprising an ultraviolet light source configured to emit UV-C light providing an irradiance dosage of at least 1.5 mJ/cm$^2$, an airflow generator configured to generate a forced airflow of at least 1000 cubic feet per minute past the ultraviolet light source, a plurality of baffles configured to introduce turbulence to the forced airflow, and wherein virus particles entrained in the forced airflow are deactivated by the ultraviolet light source.

Example 24. The ultraviolet light air purifier of any example herein, particularly example 23, wherein a virus particle in the forced airflow is exposed to the irradiance dosage for at least 0.3 seconds.

Example 25. The ultraviolet light air purifier of any example herein, particularly example 23, wherein the ultraviolet light source is a plurality of ultraviolet bulbs that extend through the baffles in the direction of the forced airflow.

Example 26. A method of treating air, comprising generating an airflow, introducing the airflow to an air treatment system through an air inlet, directing the airflow through an enclosed space defined in the air treatment system and past an array of baffles configured to impart turbulence to the airflow, exposing the airflow to UV-C light within the enclosed space for at least 0.3 s, and conveying the airflow from the air treatment system through an air inlet, wherein at least 99% of virus particles entrained in the airflow are deactivated by an exposure to UV-C light inside the air treatment system.

Example 27. The method of any example herein, particularly example 26, wherein the airflow is at least 1000 cubic feet per minute.

Example 28. The method of any example herein, particularly example 26, further comprising passing the airflow through a filter.

Each example is provided by way of explanation of the disclosure, not limitation of the disclosure. In fact, it will be apparent to those skilled in the art that various modifications and variations can be made in the preferred embodiments without departing from the scope or spirit of the disclosure. For instance, features illustrated or described as part of one embodiment can be used with another embodiment to yield a still further embodiment. Thus, it is intended that the preferred embodiments cover such modifications and variations as come within the scope of the appended claims and their equivalents.

The word "exemplary" is used herein to mean "serving as an example, instance, or illustration." Any implementation described herein as "exemplary" is not necessarily to be construed as preferred or advantageous over other implementations.

As used herein, the terms "first", "second", and "third" may be used interchangeably to distinguish one component from another and are not intended to signify location or importance of the individual components.

The terms "coupled," "fixed," "attached to," and the like refer to both direct coupling, fixing, or attaching, as well as indirect coupling, fixing, or attaching through one or more intermediate components or features, unless otherwise specified herein.

The singular forms "a", "an", and "the" include plural references unless the context clearly dictates otherwise.

Approximating language, as used herein throughout the specification and claims, is applied to modify any quantitative representation that could permissibly vary without resulting in a change in the basic function to which it is related. Accordingly, a value modified by a term or terms, such as "about", "approximately", and "substantially", are not to be limited to the precise value specified. In at least some instances, the approximating language may correspond to the precision of an instrument for measuring the value, or the precision of the methods or machines for constructing or manufacturing the components and/or systems. For example, the approximating language may refer to being within a 1, 2, 4, 10, 15, or 20 percent margin.

Here and throughout the specification and claims, range limitations are combined and interchanged, such ranges are identified and include all the sub-ranges contained therein unless context or language indicates otherwise. For example, all ranges disclosed herein are inclusive of the endpoints, and the endpoints are independently combinable with each other.

In view of the many possible embodiments to which the principles of the present disclosure may be applied, it should be recognized that the illustrated embodiments are only preferred examples and should not be taken as limiting the scope of protection. Rather, the scope is defined by the following claims. We therefore claim all that comes within the scope and spirit of these claims.

We claim:

1. A method of treating air with a movable air treatment system, comprising:
   positioning the movable air treatment system in a room, wherein the movable air treatment system has a wheeled housing with a length, a height and a width, wherein the length extends between a first end and a second end and is greater than the height and the width, the wheeled housing having an air inlet and first wheels adjacent the first end, an air outlet and second wheels adjacent the second end and an enclosed space defined between the first end and the second end, wherein the wheeled housing has a longitudinal axis extending parallel to the length and generally aligned with a floor of the room, the wheeled housing being movable via the first wheels and the second wheels to orient the air outlet in a desired direction within the room;
   generating an airflow;
   introducing the airflow through the air inlet in the wheeled housing;
   directing the airflow through the enclosed space defined in the wheeled housing and past at least one baffle in the enclosed space that is configured to impart turbulence to the airflow;
   exposing the airflow to ultraviolet light within the enclosed space for at least 0.3 s as the airflow travels at a flow rate of at least 1000 ft$^3$/minute; and
   conveying the airflow from the wheeled housing via the air outlet in the desired direction into the room; and
   wherein at least 99% of virus particles entrained in the airflow are deactivated by the exposure to the ultraviolet light inside the enclosed space of the wheeled housing.

2. The method of claim 1, wherein the airflow is directed through the housing by an air moving device.

3. The method of claim 2, wherein the air moving device is positioned at the air inlet or the air outlet of the housing.

4. The method of claim 1, wherein the housing comprises one or more side members disposed between the air inlet and the air outlet.

5. The method of claim 1, wherein the ultraviolet light has a wavelength between 100 nm and 280 nm.

6. The method of claim 1, wherein the at least one baffle comprises at least a first baffle and a second baffle.

7. The method of claim 1, further comprising directing the airflow through one or more openings in the at least one baffle.

8. The method of claim 1, wherein the ultraviolet light is supplied by one or more elongate light sources extending lengthwise in the enclosed space between the air inlet and the air outlet of the air treatment system.

9. The method of claim 1, wherein a pressure drop between the air inlet and the air outlet is 1.0 inches Water Column or less.

10. The method of claim 1, wherein the airflow travels through the movable air treatment system at an average velocity of 5 m/s or less.

11. The method of claim 1, further comprising directing the airflow through a roughing filter positioned within the movable air treatment system to remove particulates of a size ranging from 3 microns to 10 microns.

12. The method of claim 1, further comprising passing the air through a fine filter positioned within the movable air treatment system to remove particulates of a size less than 3 microns.

13. The method of claim 1, further comprising directing the airflow past a plate that partially occludes the air outlet, wherein the plate impedes air from entering the movable air treatment system through the outlet.

14. A method of treating air, comprising:
   providing an enclosure having an inlet end, an outlet end and an axis extending between the inlet end and the outlet end;
   positioning a first baffle in the enclosure closer to the inlet end than the outlet end;
   positioning a second baffle in the enclosure closer to the outlet end than the inlet end;
   arranging multiple UV light sources that emit UV-C light to extend lengthwise with respective first ends supported by the first baffle and respective second ends supported by the second baffle;
   generating an airflow at the inlet end of the enclosure;
   filtering the airflow with at least one filter positioned within the enclosure to remove particulate matter;
   directing the airflow towards the outlet end of the enclosure and past the multiple UV light sources to expose the airflow to UV-C light from within the endclosure, wherein the irradiance dosage of the UV-C light is at least 1.5 mJ/cm$^2$;
   directing the airflow past at least the first baffle and the second baffle to introduce turbulence to the airflow; and
   conveying the airflow from the enclosure and into a room;
   wherein at least 99% of virus particles entrained in the airflow are deactivated by the exposure to the UV-C light inside the enclosure.

15. The method of claim 14, wherein a virus particle entrained in the airflow is exposed to the ultraviolet light for at least 0.3 seconds.

16. The method of claim 14, wherein a virus particle entrained in the airflow moves at a linear velocity of less than 5 m/s.

17. The method of claim 14, wherein filtering the airflow to remove particulate matter is a first filtering step, wherein the first filtering step removes particulate matter sized between 3 microns and 10 microns, and wherein the method further comprises a second filtering step to remove particulate matter sized less than 3 microns.

* * * * *